United States Patent [19]

Crum

[11] Patent Number: 5,856,582
[45] Date of Patent: Jan. 5, 1999

[54] PROCESS FOR THE MANUFACTURE OF 2-HYDROXY-3-METHYLCYCLOPENT-2-ENE-1-ONE

[76] Inventor: Glen Francis Crum, 838 Eaglebrooke Dr., Ballwin, Mo. 63021-7531

[21] Appl. No.: 937,994

[22] Filed: Sep. 26, 1997

[51] Int. Cl.$^6$ .................................................. C07C 49/105
[52] U.S. Cl. ............................ 568/379; 568/355; 560/122
[58] Field of Search .................................... 568/379, 355; 560/122

[56] References Cited

U.S. PATENT DOCUMENTS 3,922,296  11/1975  McFearin, Jr. .
4,007,216   2/1977  McFearin, Jr. .
4,168,280   9/1979  Nash .

Primary Examiner—Gary Geist
Assistant Examiner—Sreenivas Padmanabhan
Attorney, Agent, or Firm—Polster, Lieder, Woodruff & Lucchesi

[57] ABSTRACT

A process for the manufacture of 2-hydroxy-3-methylcyclopent-2-ene-1-one, in which an ester of alpha-methyl glutaric acid and an ester of oxalic acid react in a polar aprotic solvent in the presence of an alkali metal alkoxide to form an intermediate compound which, after removal of said polar aprotic solvent and alcohols formed in the reaction, is hydrolyzed and decarboxylated to form said 2-hydroxy-3-methycyclopent-2-ene-1-one.

19 Claims, No Drawings

PROCESS FOR THE MANUFACTURE OF 2-HYDROXY-3-METHYLCYCLOPENT-2-ENE-1-ONE

BACKGROUND OF THE INVENTION

It is generally accepted that the natural flavor of maple sugar and maple syrup and the synthetic flavor produced by 2-hydroxy-3-methylcyclopent-2-ene-1-one are the same and that the responsible compounds are the same compounds. The synthetic flavor compound is often called maple lactone because of its flavor and because of its existence in maple sugar and other maple products even though it is not truly a lactone, that name having been given before its chemical structure was known.

Maple lactone finds immediate and practical utility as a flavoring agent in the preparation of maple syrup and other artificially flavored maple products Because some the sources of natural maple flavoring substance have declined and because the number of people who consume maple products has increased, there is a need for efficient and economical methods for producing maple lactone.

The Dieckmann reaction for producing maple lactone is disclosed in U.S. Patent No. 3,922,296 issued to McFearin (hereinafter McFearin '296). The McFearin process requires a step of adding methyl bromide, which adds to the cost and complexity of the process, and adds to the waste disposal expense. Several of the U.S. Patents which the inventors hoped would be useful toward the end of preparing maple lactone or related compounds are discussed in McFearin '296.

BRIEF SUMMARY OF THE INVENTION

Accordingly, an object of this invention resides in the provision of an improved process for the preparation of 3-methyl-cyclopentane-1,2-dione which is both economically and commercially feasible and utilizes a source of a starting material not employed by the prior art processes of McFearin '296.

The present invention is directed to an improved process for the manufacture of 2-hydroxy-3-methylcyclopent-2-ene-1-one by the condensation of esters of alpha-methyl glutaric acid and oxalic acid in a polar aprotic solvent in the presence of an alkali metal alkoxide, removing the solvent, hydrolyzing the remainder, and removing carbon dioxide to form 2-hydroxy-3-methylcyclopent-2-ene-1-one, which is often called by its tautomeric form, 3-methylcyclopentane-1,2-dione [CAS No. 765-70-8].

The present invention is similar to McFearin '296 in some of the chemical steps. However, the difference presented in the present invention is an improvement in the process of McFearin '296.

The starting material for the present invention, dimethyl alpha-methyl glutarate, has become widely available as a by-product of another industrial process, specifically in the manufacture of Nylon 6-6. The present invention therefore provides a simple and inexpensive route to the production of maple lactone.

U.S. Pat. No. 4,168,280 issued to Nash (hereinafter Nash '280) uses an alpha-alkyl glutarate ester as the starting material. However, the method for converting the open chain glutarate to the cyclopentyl configuration uses metallic alkali metal as a reducing agent in an acyloin condensation. Thus, this patent is not the same as the present invention, which uses oxalate ester and an alkoxide of an alkali metal to form the methyl cyclopentane dione.

DETAILED DESCRIPTION OF THE INVENTION

As has been pointed out above, the present invention relates to the preparation of maple lactone, or 3-methylcyclopent 1,2 dione, which may be represented by the following general formula:

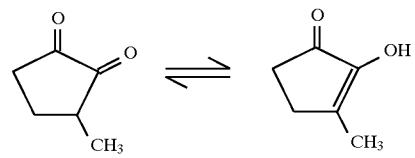

This formula represents both the desired molecule and the 1-hydroxy tautomer, 2-hydroxy-3-methylcyclopent-2-ene-1-one, which exists contemporaneously with the desired molecule.

The preparation of the maple lactone contemplated by the present invention uses dimethyl alpha-methyl glutarate ester as the starting material.

The process employed in the present invention is essentially set out in U.S. Pat. No. 3,922,296 issued to McFearin (hereinafter McFearin '296) which is herein incorporated by reference. Unlike McFearin '296, however, the use of dimethyl alpha-methyl glutarate ester as a starting material instead of dimethyl glutarate allows for the omission of the step of adding methyl bromide found in McFearin '296. Thus the reaction may be represented as follows:

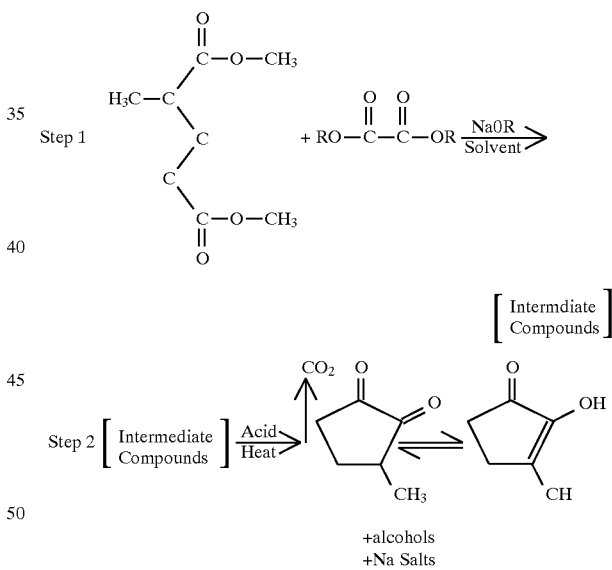

+alcohols
+Na Salts where R is a lower alkyl (one to three carbons), and where the solvent employed is a non-aqueous aprotic polar solvent such as dimethyl formamide (DMF). It is contemplated by the present invention that any of a number of non-aqueous aprotic solvents may be used, in particular N-methylpyrrolidone may be preferred because of safety and environmental considerations.

Numerous variations in the process of this invention will occur to those skilled in the art in the light of the foregoing disclosure.

I claim:

1. A process for the manufacture of 2-hydroxy-3-methylcyclopent-2-ene-1-one, comprising reacting an ester of alpha-methyl glutaric acid and an ester of oxalic acid in a polar aprotic solvent in the presence of an alkali metal alkoxide to form an intermediate compound, removing said polar aprotic solvent and alcohols formed in the reaction, and hydrolyzing and decarboxylating said intermediate to form said 2-hydroxy-3-methylcyclopent-2-ene-1-one, the process being carried out without a step of alkylating said intermediate.

2. The process of claim 1 in which the ester of alpha-methyl glutaric acid is the methyl ester.

3. The process of claim 1 in which the ester of alpha-methyl glutaric acid is the ethyl ester.

4. The process of claim 1 in which the ester of oxalic acid is the methyl ester.

5. The process of claim 1 in which the ester of oxalic acid is the ethyl ester.

6. The process of claim 1 in which the alkali metal alkoxide is sodium methoxide.

7. The process of claim 1 in which the alkali metal alkoxide is sodium ethoxide.

8. The process of claim 1 in which the polar aprotic solvent is dimethylformamide.

9. The process of claim 1 in which the polar aprotic solvent is N-methylpyrrolidone.

10. A process for the manufacture of 2-hydroxy-3-methylcyclopent-2-ene-1-one consisting essentially of reacting an ester of alpha-methyl glutaric acid and an ester of oxalic acid in a polar aprotic solvent in the presence of an alkali metal alkoxide to form an intermediate compound, removing said polar aprotic solvent and alcohols formed in the reaction, and hydrolyzing and decarboxylating said intermediate to form said 2-hydroxy-3-methylcyclopent-2-ene-1-one.

11. The process of claim 10 in which the ester of alpha-methyl glutaric acid is the methyl ester.

12. The process of claim 10 in which the ester of alpha-methyl glutaric acid is the ethyl ester.

13. The process of claim 10 in which the ester of oxalic acid is the methyl ester.

14. The process of claim 10 in which the ester of oxalic acid is the ethyl ester.

15. The process of claim 10 in which the alkali metal alkoxide is sodium methoxide.

16. The process of claim 10 in which the alkali metal alkoxide is sodium ethoxide.

17. The process of claim 10 in which the polar aprotic solvent is dimethylformamide.

18. The process of claim 10 in which the polar aprotic solvent is N-methylpyrrolidone.

19. A process for the manufacture of 2-hydroxy-3-methylcyclopent-2-ene-1-one comprising a condensation reaction between a lower alkyl ester of α—methyl glutarate and a lower alkyl ester of oxalic acid to form an intermediate, followed by a step of converting the intermediate to said 2-hydroxy-3-methylcyclopent-2-ene-1-one.

* * * * *

UNITED STATES PATENT AND TRADEMARK OFFICE
CERTIFICATE OF CORRECTION

PATENT NO. : 5,856,582
DATED      : January 5, 1999
INVENTOR(S) : Glen Francis Crum It is certified that error appears in the above-identified patent and that said Letters Patent is hereby corrected as shown below:

Col. 2, line 50
  replace "second CH"
  with --CH with subscript 3 after CH--.

Signed and Sealed this

Fourth Day of May, 1999

Attest:

Attesting Officer

Q. TODD DICKINSON

Acting Commissioner of Patents and Trademarks